(12) United States Patent
Sawyer et al.

(10) Patent No.: US 9,527,758 B1
(45) Date of Patent: Dec. 27, 2016

(54) MOLLUSK REPELLANT AND METHODS OF WATER TREATMENT

(71) Applicant: 060Bio, LLC, San Clemente, CA (US)

(72) Inventors: John Edward Sawyer, Charleston, WV (US); Paul Gregory Coxe, Bellville, OH (US)

(73) Assignee: 060 Bio, LLC, Bellville, OH (US)

( * ) Notice: Subject to any disclaimer, the term of this patent is extended or adjusted under 35 U.S.C. 154(b) by 197 days.

(21) Appl. No.: 14/207,097

(22) Filed: Mar. 12, 2014

Related U.S. Application Data

(60) Provisional application No. 61/778,415, filed on Mar. 13, 2013.

(51) Int. Cl.
| | |
|---|---|
| *A01N 25/16* | (2006.01) |
| *A01N 59/20* | (2006.01) |
| *C02F 1/50* | (2006.01) |
| *C02F 1/68* | (2006.01) |
| *C02F 103/00* | (2006.01) |
| *C02F 103/08* | (2006.01) |

(52) U.S. Cl.
CPC ............... *C02F 1/50* (2013.01); *A01N 25/16* (2013.01); *A01N 59/20* (2013.01); *C02F 1/505* (2013.01); *C02F 1/687* (2013.01); *C02F 2103/007* (2013.01); *C02F 2103/008* (2013.01); *C02F 2103/08* (2013.01)

(58) Field of Classification Search
CPC ............. C02F 1/50; C02F 1/505; C02F 1/288; C02F 1/685; C02F 1/687; C02F 1/688; C02F 2103/007; C02F 2103/008; C02F 2103/08; A01N 25/16; A01N 59/20; C08J 9/365; C08J 2205/06

See application file for complete search history.

(56) References Cited

U.S. PATENT DOCUMENTS

| | | | |
|---|---|---|---|
| RE32,356 E * | 2/1987 | Cardarelli | ............... C08J 9/26 514/128 |
| 4,642,192 A | 2/1987 | Heskett | |
| 5,122,274 A | 6/1992 | Heskett | |
| 5,135,654 A | 8/1992 | Haskett | |
| 5,198,188 A | 3/1993 | Holt | |
| 5,269,932 A | 12/1993 | Haskett | |
| 5,275,737 A | 1/1994 | Heskett | |
| 5,314,623 A | 5/1994 | Heskett | |
| 5,415,770 A | 5/1995 | Heskett | |
| 5,433,856 A | 7/1995 | Haskett | |
| 5,510,034 A | 4/1996 | Haskett | |
| 5,599,454 A | 2/1997 | Heskett | |
| 5,827,434 A * | 10/1998 | Yando | ............... C02F 1/505 137/268 |
| 5,833,859 A | 11/1998 | Heskett | |
| 5,837,134 A | 11/1998 | Haskett | |
| 5,951,869 A | 9/1999 | Haskett | |
| 6,197,204 B1 | 3/2001 | Heskett | |
| 2002/0006867 A1 | 1/2002 | Ponder | |
| 2005/0232960 A1* | 10/2005 | Buccolini | ............... C02F 1/50 424/405 |

(Continued)

OTHER PUBLICATIONS

P.O. No. 1024, Jun. 25, 2003, (not patent document).

*Primary Examiner* — Lucas Stelling

(74) *Attorney, Agent, or Firm* — Favorito Law, LLP

(57) ABSTRACT

An apparatus comprising copper and zinc adhered to reticulated foam is useful for repelling or preventing mollusk infestation.

10 Claims, 1 Drawing Sheet

(56) References Cited

U.S. PATENT DOCUMENTS

| | | | |
|---|---|---|---|
| 2006/0182944 A1* | 8/2006 | Leavitt | C02F 1/288 |
| | | | 428/304.4 |
| 2010/0307978 A1 | 12/2010 | Sawyer | |
| 2011/0062065 A1* | 3/2011 | McCague | C02F 1/001 |
| | | | 210/167.1 |
| 2012/0018384 A1 | 1/2012 | Sawyer | |

* cited by examiner

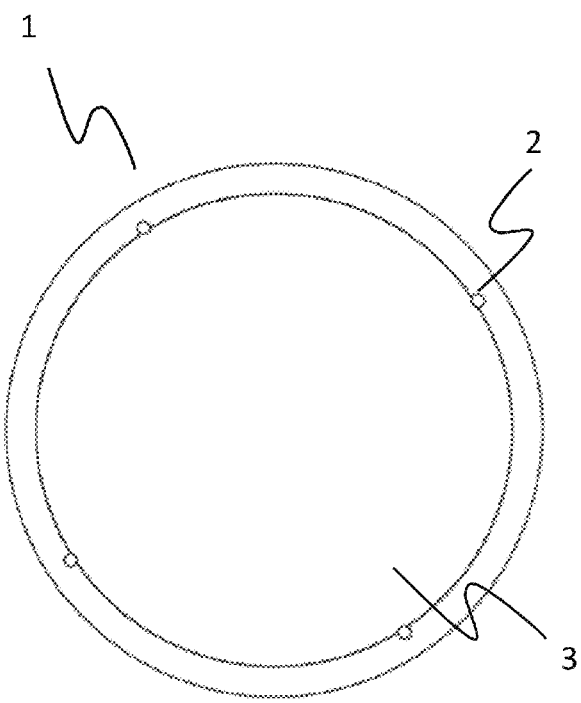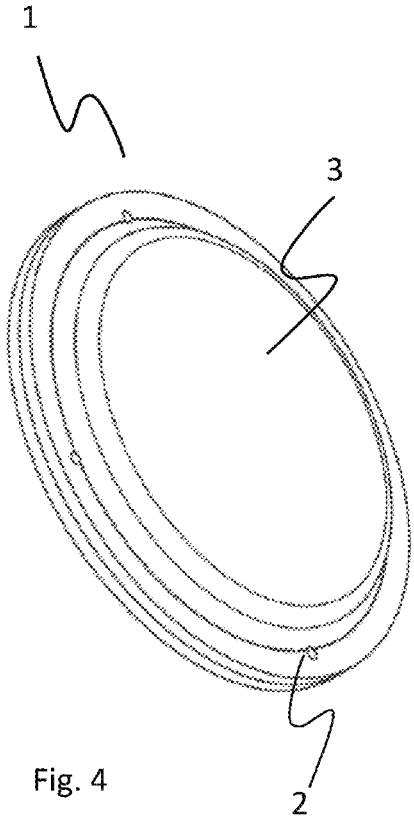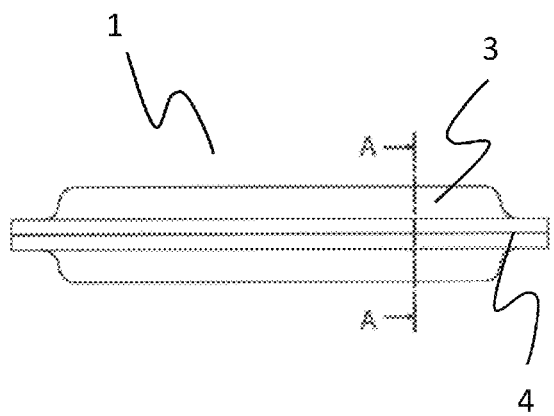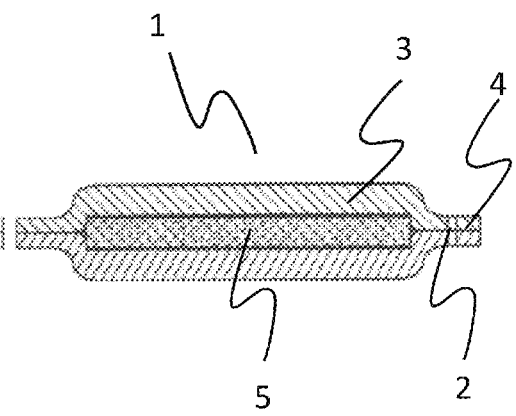

# MOLLUSK REPELLANT AND METHODS OF WATER TREATMENT

This application claims priority to U.S. Provisional Application No. 61/778,415, filed Mar. 13, 2013, which is incorporated herein by reference in its entirety.

BACKGROUND

Field

The field relates to antifouling water treatment agents and repellent devices, particularly for treating or preventing infestation of mollusks such as zebra or quagga mussels.

Description of the Related Art

The invasive species of *dreissena polymorpha* (zebra mussels) and *Dreissena rostriformis bugensis* (quagga mussels) were first reported in the US in 1988, according to the USGS. Since 1988 the spread has been rapid in spite of control efforts. (Benson, A. J. 2011. Zebra mussel sightings distribution. Retrieved Oct. 29, 2012 from http://nas.er.usgs.gov/taxgroup/mollusks/zebramussel/zebramusseldistribution.aspx.) The annual costs to address this issue were estimated several years ago at 267 million dollars per year (Environ Manage. 2007 July; 40(1):105-12. Epub 2007 May 24.) This cost makes the control of these aquatic invasive species an economically important process.

Conventional control methods include heat, chemicals such as chlorine, and use of surface coatings. The immature mussels, called veligers, attach to some surfaces much more easily than others. For instance, wood and cotton rope are colonized much faster than metals. However, even metal surfaces may be colonized in time. A method of continuously repelling both adult mussels and veligers is needed.

US Pat. Appl. No. 2010/0307978 provides an apparatus and method for contaminant removal from an aqueous solution. A permeable reactive barrier and an effective method of removing contaminants from water using adsorbent powders, such as zero valent iron particles, adhered throughout a reticulated foam structure are provided. These contaminants can include, but are not limited to: selenium, perchlorate, chromates, halogenated organic compounds, aluminum, lead, copper, technetium and arsenic. The zero valent iron apparatus exemplified therein does not repel or prevent mollusk infestation.

Cuprous oxide and zinc oxide, which are commercially used antifoulants, function by releasing heavy metals, i.e., copper and zinc, a harmful toxin, especially in the marine environment.

It would be helpful to the field to overcome the toxicity issues related to antifouling agents, while maintaining the effectiveness of such treatments.

SUMMARY

In some aspects, a method comprises repelling or preventing infestation of mollusks in a body of water infested with mollusks or at risk of infestation by mollusks with a repellant comprising copper and zinc fines (CuZn fines or CuZn particles) adhered to a reticulated foam substrate. The repelling or preventing step further comprises: contacting the repellant with the body of water for a time sufficient to repel or prevent infestation by the mollusks; wherein the zinc solubilizes during the contacting step in an amount sufficient to repel or prevent infestation by said mollusks; and wherein the copper remains substantially adhered to the reticulated foam substrate during the contacting step. Mollusks such as invasive mussels e.g., zebra mussels or quagga mussels are susceptible to treatment. In some cases the body of water is infested with zebra mussels or quagga mussels.

The repellent may include copper and zinc fines adhered to the reticulated foam substrate with a water resistant adhesive. In some aspects, the zinc is present in the copper and zinc fines in an amount greater than the maximum saturation concentration of zinc in a copper and zinc solid solution, such as about a weight ratio of zinc/copper greater than about 43/57 weight ratio.

Various bodies of water include fresh water bodies such as lakes, channels, or rivers that may be infested with or at risk of infestation with mollusks such as zebra mussels or quagga mussels. The bodies of water may be proximate a marina, bridge pylon, channel breakwall, lock, or dock or other structures found in the water. For example, the repellant may be positioned proximate a bridge.

The repellent may also further comprise a protective outer covering. The reticulated foam substrate may be disposed within said outer protective covering. Copper and zinc fines may be adhered to the reticulated foam substrate. The copper and zinc fines may be exposed on the surface of the reticulated foam substrate when adhered thereto. The protective outer covering may comprise a reticulated foam wherein the pore size of the reticulated foam of the protective outer covering is smaller than the pore size of the reticulated foam substrate. In other aspects, the protective outer covering comprises a plastic mesh.

These and other embodiments are described below in more detail.

BRIEF DESCRIPTION OF THE DRAWINGS

FIG. 1 illustrates an embodiment of front view of an encased treated substrate that may be used in various applications herein.

FIG. 2 illustrates an isometric view of the embodiment of FIG. 1.

FIG. 3 illustrates a side view of the embodiment of FIG. 1.

FIG. 4 illustrates a cross-sectional view along the A-A axis identified in FIG. 3.

DETAILED DESCRIPTION OF THE PREFERRED EMBODIMENT

To address the mollusk infestation issue, is been found that small amounts of ions can be used to prevent infestation by or repel mollusks such as adult mussels as well as veligers, without causing toxicity issues. Low concentrations of zinc ions prevent the attachment of mussels for an extended time, without releasing significant amounts of copper.

Foam may provide a high surface area material with good mass transfer characteristics. The material may contain one or more substrates, that may form the treated substrate(s) 5 (see FIG. 4), to which the CuZn fines are adhered. In some aspects, a reticulated foam substrate is used. The reticulated foam substrate may be rated to have a range of surface areas, for example, about 5-20 pores per inch (ppi), such as about 10-15 ppi or 10 ppi. Higher rated ppi foams have smaller pores and thus have a greater surface area. In some aspects, higher rated ppi foams increase the time in which the treated substrate remains effective due to greater amount of fines that adhere to the foam. However, much higher rated ppi foams, e.g., over 30 ppi, have small pores that prevent fines from entering the open cell structure after adhesive is applied. In addition, much higher ppi foams slow water flow through the treated substrate, which may reduce effectiveness of the treated substrate. Relatively lower ppi foam allows a greater flow rate of the water, thereby increasing the effectiveness of the treated substrate by allowing the zinc to solubilize and travel to a location that will repel mollusks. Further, environmental conditions, i.e., temperature of water, current, sunlight etc. may affect the overall effectiveness of the treated substrate. In some aspects, the range of ppi of foams herein, such as a foam of about 10 ppi are effective for many applications over a wide range of environmental conditions.

Reticulated foams, such as polymeric reticulated foams, are commercially available. The reticulated foam herein may comprise various polymers such as standard poly ether or poly ester urethane. The foam may be chemically treated by dipping (quenching) foam or by means of a thermal gas explosion (zapped) within a containment chamber, converting the foam from a closed cell to open cell foam. During the foam treatment process, the cells are burned off leaving gaps in between them which are then measured and rated by ppi (pores per inch). In some aspects, an approximately 10 ppi reticulated foam may be used based on the size of the CuZn particles and the amount of CuZn fines that may be loaded on the cell membranes. The foam may be commercially available from companies such as Foamex, Regicell, Crest, or Woodbridge. A normal closed cell polyurethane, which is not breathable, i.e., prevents air or water to flow through it, begins in the form of a bun, which has an outer skin that needs to be removed, to enable the zapping process to form open cells. Various machines may be used to cut reticulated foam disks such as a die cutter, a computer aided design (CAD) machine fitted with a knife blade, or a horizontal band saw that may use a continual wire or saw blade.

In some aspects, the reticulated foam is unstructured and is not a reticulated foam structure having a sponge-like structures of metal or ceramics, such as a foamed substrate formed of zinc or copper in accordance with U.S. Pat. No. 5,759,400. Unlike polymeric reticulated foam that may be used herein, U.S. Pat. No. 5,759,400 refers to polyethylene as "foreign matter" in a substrate; a foam structure of metal differs from reticulated foam herein such as unstructured and/or polymeric reticulated foam.

The thickness of the substrate, that may form the treated substrate 5 (see FIG. 4), may vary. For example, in some aspects, the thickness of the substrate may be about 7 inches or less, such as about ⅛ to 5 inches or about ¼ to 3 inches. In some aspects, the substrate may have a thickness of about ½ to 1 inch or about ½ inch. In some aspects, the thickness may be the average thickness if the material is not uniformly thick. In some aspects, using foam having less thickness such as less than 3 inches, allows more thorough saturation with the adhesive and fines. Various adhesives suitable for adherence to reticulated foam and having good water resistant properties may be used to adhere the CuZn fines to the reticulated foam. Examples include urethane adhesive, siliconized acrylic adhesive, or acrylic polymer adhesive. In some aspects, the adhesive includes an acrylic polymer adhesive such as latex adhesive emulsion suitable for reticulated polyurethane foam. DAP Inc. manufactures a latex adhesive emulsion suitable for the disks. The adhesive may be applied using various conventional techniques such as dipping. In some aspects, approximately ½-3 g may be used per cu. inch of reticulated foam. For example, in some aspects, a 6 inch diameter disk that is ½ inch thick is coated with approximately 1-2 g/cu.inch or about 12-15 g of adhesive. The solvent will be removed during drying so the weight attributed to the adhesive in the dried product will be lower.

The process of coating the foam with CuZn fines may be referred to as loading the fines or coverage with the fines. The CuZn fines may be applied by various methods such as dipping the adhesive-coated substrate into the fines, by dusting, using a sifter-like apparatus or coating by other conventional methods. In some aspects, the substrate is coated until the coated substrate cannot hold any more of the fines.

Once the CuZn fines are adhered, the treated substrate may be dried. Drying times may vary due to external environmental conditions such as temperature and humidity. In some aspects, the drying time typically may take approximately 24 to 36 hours.

Although the fines may be added to the adhesive and then applied as a slurry, such a method reduces the effectiveness of the treated substrate during use. When the adhesive is applied first and then CuZn fines are loaded over the adhesive, it is believed that the increased exposure of the CuZn fines on the surface of the substrate in the water improves the effectiveness of the treated substrate.

Copper zinc fines or CuZn fines are used as the active ingredient in the treated substrate. Copper zinc fines refer to a copper and zinc mixture of particles. Zinc inherently forms a solid solution with the copper to form a high zinc content brass until maximum saturation. In some aspects, a 50/50 by weight copper zinc mixture is used wherein the copper zinc particles form a combination of brass particles until maximum saturation. The maximum saturation ratio of zinc to copper by weight is about 43 to 57. Once the maximum saturation of zinc dissolved in the copper is reached, undissolved zinc particles may remain throughout the mixture that have not been dissolved in the copper. Without being bound by theory, undissolved zinc particles in the copper zinc particle mixture appear to provide at least most or substantially all of the repellant activity. Thus, in some aspects, the weight ratio of Zn/Cu is greater than about 43/57 by weight. Thus, in some aspects, brass materials having a relatively low level of zinc are less or not effective, i.e., wherein the Zn/Cu weight ratio is less than about 43/57, or wherein a concentration beyond maximum saturation has not been reached. Thus, in a 50/50 weight ratio particle mixture of Cu/Zn, about 38% by weight of the zinc is dissolved in 50% by weight of the copper, leaving about 12% by weight of free zinc in the solid phase that remains undissolved in the copper. Also, the zinc rich surface, which is in intimate contact with copper, provides a galvanic corrosion cell to allow the formation and dissolution of zinc ions into the water. Without being bound by theory, a sufficient amount of copper forms the galvanic corrosion cell with the zinc. In some aspects, at least about 20% by weight of copper in a zinc and copper particle mixture may be sufficient to provide a galvanic corrosion cell activity. In some cases, about 20-50% by weight of copper in a copper and zinc mixture is sufficient to provide galvanic corrosion cell activity.

In some aspects, KDF 55 copper zinc fines are used that have a 200 mesh size. However, use of other mesh size is contemplated, although relatively smaller particles provide a greater surface area and are more readily absorbed into the foam by the adhesive. Larger mesh sizes of the copper zinc fines tend to plug the pores of the foam thereby reducing the effectiveness of the treated substrate during use. The mesh size is roughly equivalent to the number of holes per square inch in a screen through which the particles fall through. Thus, relatively fewer holes per inch means the particles may have a relatively larger particle size. The mesh size, which is approximately equivalent to holes per square inch, may be approximately equivalent to the number of pores per inch in the foam. Thus, in some aspects, the mesh size of the particles is greater (i.e., particles are smaller) than the pores per inch of the foam substrate. For example, 30-40 mesh size of particles may be used with a 10 ppi foam because the particles are smaller than the foam's pore size. Thus, in some aspects, about 30 or greater mesh sized particles may be used, for example, about 30-500, 40-400, 50-300 or 100-200 mesh sizes may be used, for example, with a 10 ppi foam.

The rate of zinc ion introduction is somewhat dependent on pH, and with normal, nearly neutral, pH values in most applications in which the product will be used, the dissolution rate is adequate to repel mussels. At lower pH values the dissolution rate is higher, leading to a shorter protection time.

During use, the treated substrate comprising the copper zinc fines loses zinc and its concomitant mass. The treated substrate is spent when the zinc release drops to zero or about zero due to the complete or about complete loss of the zinc rich solid phase (i.e., zinc that is not dissolved in the copper) in the starting material. At this spent state the treated substrate has mainly copper and dissolved zinc remaining, together with any scavenged heavy metals sequestered from the water.

Depending on the size of the substrate and the amount of CuZn fines with which it is treated, the amount of water and the length of active treatment time may vary. For example, it is expected that a substrate of approximately the size made in the example may treat at least about 12 to 15 cubic feet of water effectively for at least about 7 to 9 months depending on the environmental conditions, i.e., temperature of water, current, sunlight etc. In some cases, the treated substrate will remain effective for about one year and in some cases about four years. The treated substrate 5 may be used "as is" to treat water, without the outer covering 3 shown in FIGS. 1-4. To further protect the integrity of the treated substrate during use, the treated substrate may be positioned as an inner pad or core 5 having an outer covering 3. In addition, the protective outer covering 3 may prevent particles of foam that may become dislodged during use to escape into the treated water.

In some aspects, the treated substrate may contain a protective outer material 3 in FIGS. 1-4 such as a reticulated foam material or a water permeable fabric to protect the inner disk and increase residency time of the water with the treated substrate, while simultaneously allowing water to freely move through it under various environmental conditions when in use. For example, the outer casing may be selected based on the particular area, such as in areas where the water flow has a slow but steady current.

The outer casing 3 may be made from reticulated foam that encases the treated substrate. The reticulated foam may be made by the process described above. Various different surface area foams such as about 40-50 pores per inch (ppi), e.g., about 45 ppi may be used. It has been found that using reticulated foam with higher surface area and higher pores per inch may restrict water flow. For example in stagnant water or applications where the water current is extremely slow a 60 ppi foam may be too dense to allow water to flow freely through, thereby impeding the function of the treated substrate. Nonetheless, without being bound by theory, in some aspects, e.g., using great than 40 ppi but less than 60 ppi reticulated foam, some water restriction is beneficial to allow the untreated water sufficient residency time proximate the treated substrate. Increased residency time, without being bound by theory, may also act to slow dissipation of the zinc ions and increase the life of the treated substrate. In addition, using a high surface area foam may cause the covering to act unfavorably as a sponge instead of as a sieve. Alternatively, if 20 or 30 ppi foam is used, the water flow may be suitable, however, the material may be too insubstantial to withstand the environmental conditions to which it is exposed. In addition, using a low ppi foam may be ineffective for fusing to the treated substrate, resulting in inferior protective properties. In some aspects, the approximately 45 ppi reticulated foam may be sufficiently versatile among various treatment scenarios because it allows a good flow through rate, provides good protection of the inner disk, and fuses properly when placed under heating conditions during the manufacturing process.

The reticulated foam casing 3 also prevents copper zinc particles from being released into the water, which may cause problems with machinery such as engines and water intake systems.

The outer casing 3 may be made from other materials, or in addition to a first outer casing such as an outer foam casing, for use in harsh conditions. Harsh conditions may include treatment scenarios involving larger faster flows, for example intake lines used in water and power plants. In higher flow rate scenarios, the outer casing may allow water to flow through it allowing the inner core to work, while providing better protection for the treated substrate, but also provides water flow restriction so that residency time of the water proximate the treated substrate is increased. In some aspects, water permeable material, such as textiles or woven or nonwoven fiber may be used, which allow water flow through them. The water permeable material may be made from a geosynthetic material or polypropylene. In some aspects, a geotextile such as the Mirafi RSI Series may be used, which has other applications such as underwater construction where the material retains its shape after exposure to a battery of environmental conditions. Geotextiles may be made using a woven geosynthetic fiber or fibers that are punched or otherwise manipulated to provide water permeability. The Mirafi S Series material acts similarly to geotextiles but comprises polypropylene fiber. Other material comprising polyester, such as 100% polyester with a polyvinyl coating, may be used, which has applications related to outdoor furniture.

In certain embodiments, materials used for the outer casing for repelling mollusks and other uses herein, may be unsuitable for very high flow water. For example, in some aspects, the presently contemplated outer casings may be unsuitable for water that is filtered or pumped through a relatively small pipe because the water-flow restrictive outer casings herein may strain filters or motors that are pulling or pushing water that must travel through the outer casing. For example, in some aspects, when water is pumped and/or filtered in water delivery systems such as in pools or home use within a relatively small pipe, a water-flow restrictive outer casings herein when located inside such a small pipe may cause increased pressure by very high water flow flowing through thereby disadvantageously slowing the volume of water to be treated, which may compromise machinery, such as pumping or filtering apparatuses. Thus, in some aspects, these uses and materials that may cause these types of problems may be excluded in the materials and uses herein.

Various materials may be used to enclose or seal the outer casing such as stitching, e.g., nylon stitching, or fasteners such as snaps or buttons. In some aspects, a heat activated film 4 is used to form a strong bond during the fusing process of a reticulated foam outer core to encase the inner core. Various machines may be used as known in the art to cut the heat activated film 4, for example, a die cutter, or a CAD driven table and knife. In some aspects, the fusing material is used on the outer edges of the casing to house the treated substrate therein.

In addition, fasteners may be used to suspend the treated substrate or the encased treated substrate 1 in water using, for example, a parachute cord attached to the dock by an eyebolt. In some aspects, the treated substrate or the encased treated substrate may be otherwise immobilized or partially immobilized such that it remains relatively stationary when submerged in water. For example, the treated substrate or the encased treated substrate may be attached directly to a submerged or partially submerged object, such as a pylon, break wall, or buoy. Openings or holes 2 may be placed on the edge of the casing to allow fastening thereto. In addition, a weight may be added to anchor the treated substrate e.g., in a relatively stationary and/or vertical position. For example, a small bag of rocks may be attached to the substrate or an encased treated substrate, such as by using a bag of rocks clipped through an opening on the edge thereof.

In some aspects, a minimal amount of copper is leached from the apparatus during use. Under certain conditions dependent in part on length of use, copper may be leached in an amount of 0.010 mg/l to 0.15 mg/l, approximately 0.16 mg/l to 0.20 mg/l or approximately 0.21 mg/l to 0.25 mg/l.

The terms "approximately, "about," and "substantially" as used herein represent an amount close to the stated amount that still performs the desired function or achieves the desired result. For example, the terms "approximately," "about" and "substantially" may refer to an amount that is within less than 10% of, within less than 5% of, within less than 1% of, within less than 0.1% of, and within less than 0.01% of the stated amount.

The repellent may be made by various methods and are not limited to the examples provided herein.

EXAMPLES

Example 1

Treated Substrate

S-10 grade bun stock of reticulated nominal 10 pores per inch poly ester polyurethane foam in a charcoal color having a nominal density of 1.9 lb/cu.ft was obtained from Crest Foam Industries, Inc. The skin from a bun of 10 ppi reticulated foam prepared using a zapped process was cut using a ferry band saw and leveled in sheets to a specific thickness of ½"+tolerance–zero.

The leveled sheets were placed on a machine and about 250 6" diameter disks were cut. Each of the 6" disks were dipped in a DAP acrylic polymer adhesive and the excess glue removed. Approximately, 12-15 g of glue was applied to each disk. KDF Cu Zn Process Media fines 200 mesh size were applied by dusting, using a sifter until approximately 80 to 90 grams of fines were bonded to disk, and the disk did not hold any more of the fines. The dipped and dusted disks were set on drying racks to dry for approximately 24 to 36 hours. The treated substrate may be used "as is" to treat water.

Example 2

Slurry-Treated Substrate

The disks were cut using the same process as Example 1. DAP acrylic polymer adhesive and KDF Cu Zn Process Media fines 200 mesh size were mixed to form a slurry. The slurry was applied to the disks and the excess removed, and the slurry treated disks were dried.

Example 3

Encasing the Treated Substrate

To protect the integrity of the treated substrate during use, an outer covering was made, as illustrated in FIGS. 1-4. Regicell 45, an approximately 40-50 ppi pore count thermally reticulated polyester foam was obtained from Woodbridge Foam Partner. The Regicell 45 reticulated foam was cut to size using the same process as the 10 ppi foam above.

Two pieces of 45 ppi foam was cut into approximately 7½" or 7¾"×³⁄₁₆" diameter disks for creating the outer pads or casing 3 of the pouch. The disks were cut with 4 holes 2, ¼" in diameter, 90 degrees apart for hanging the pouch during use in various applications.

A roll of thin heat activated film 4, Syntac BF50, a thermoplastic film that is used to fuse polyurethane foams was cut using a die cutter into ring disks having a 7¾" outer diameter (OD) with a 6¼" inner diameter (ID).

The 45 ppi foam disk was placed in a heat platen jig used for holding parts together while they are being sealed. The 10 ppi Cu Zn coated disk 5 was placed in the jig on top of the 45 ppi foam disk 3. The heat activated film ring was placed in the jig adjacent the edge of the 45 ppi foam. A second 45 ppi foam disk then was placed on top and the edges thereof were proximate the heat activated disk 4, where the holes 2 in the 45 ppi foam outer casing disks were aligned. The platen jig was closed and the heat was set at 225° F. for 25 seconds to fuse the outer edges of the 45 ppi foam disks to each other thereby encasing the treated disk 5 and forming a pouch 1. The pouch 1 was let to stand until cool. After cooling the pouch was ready for use.

Example 4

Method of Using the Treated Substrate to Repel Mollusks

Example 4a)

Lake Oohlagah, OK

Four disks made by a process similar to the process in Example 1 described above, each comprising a three inch diameter by one inch thick reticulated foam having 30 pores per inch nominal pore size, were suspended in fresh water, Lake Oohlagah, OK, infested with zebra mussels. The four disks comprised a copper/zinc treated disk ("treated disk"), a brass treated disk ("brass disk"), and two untreated disks, i.e., two plain foam disks without copper/zinc or other metal treatment. The four disks were suspended by an approximately 2-3 foot cord or chain from a PVC rod to maintain separation of approximately 16 inches, in the order of two untreated disks, one treated disk and one brass disk. Zebra mussel colonization was found on the two untreated disks after seven months. No mollusk colonization, such as zebra mussel colonization, was found on the treated disk or the brass disk. Colonization of mussels on brass has been reported, but surprisingly, the brass disk was not infested. Without being bound by theory, it is believed that because the brass disk contains the maximum saturation level of zinc or less, i.e., at or less than 43/57 weight ratio of Zn/Cu, there was little or no zinc rich solid phase to dissolve into the water and cause the repellant activity. However, in this experiment, the brass disk was in the zone of protection of the treated disk so no colonization was found. In addition, the untreated disk that was in a closer proximity to the treated disk had fewer zebra mussels than the disk that was farther. In addition the cord on the treated disk was not infested while the untreated chains were infested. Thus, it was surprising to find a zone of protection of at least about a 1-2 feet radius around the disk.

The disks made by the process of Example 2 were tested under similar conditions. The efficacy of the slurry treated disks made by the process of Example 2 was approximately 15% as effective as the treated disks made by the process of Example 1.

Example 4b)

Lake Murray, OK, Zebra Mussels

Lake Murray in Oklahoma was officially recognized as harboring invasive zebra mussels (*dreissena polymorpha*) in May of 2012. Since then, the mussels have rapidly multiplied, as is typical with this species once an invasion begins.

Among other uses, lake water from Lake Murray was used to irrigate the grass and shrubs surrounding the Nature Center at Tucker Tower in Lake Murray in OK. The 4-inch diameter intake pipe used to collect the lake water for irrigation has a vented end that serves to prevent large debris from entering the irrigation system and disrupting the flow of water. The pipe is positioned approximately six feet below the surface of the lake, and may be closer or farther from the surface depending on the lake level.

Before the zebra mussel invasion in May 2012, the intake pipe and irrigation pump were virtually maintenance free and typically could be left alone for months without clogging.

Several months after the invasion, the zebra mussels began to attach to and cover the intake pipe internally and externally (among other structures in the lake). As a result, the flow of water was impeded, which significantly compromised the functioning of the irrigation system. Thereafter, regular maintenance was required to remove the mussels from the intake pipe so that water could flow freely through it and adequately supply the irrigation system. Thus, approximately every 4 to 6 weeks, mussels were either manually scraped off by hand or the pipe was removed from the lake where the mussels were left to die before returning the intake pipe to the lake.

In an attempt to reduce the significant, above-described maintenance issues posed by the zebra mussel invasion, one apparatus made in accordance with Example 1, was hung in the lake just above the submersed vented end of the intake pipe, approximately 6 feet below the water's surface. Water temperatures in Lake Murray at the depth of the apparatus ranged from about 80 F or more in the summer to just above freezing in the winter. The apparatus was weighed down with rocks to immobilize it proximate the intake pipe. Within 2 weeks of the apparatus's installation, the intake pipes were inspected and no mussels were observed in the area immediately surrounding the apparatus. After approximately 4 months in the water, a large area having approximately a 5'-7' radius around the apparatus and around the intake pipe was devoid of mussels.

Example 4c)

Lake Mead, NV, Quagga Mussels

Lake Mead, NV, officially reported quagga mussel (*dreissena rostriformis bugensis*) invasion in 2007. It has been estimated that the total of adult quagga mussels in Lake Mead is 50 trillion, based upon the lake square footage and the prolific spread of the mussel, with veligers (larvae) exceeding this number.

A ski boat was kept in a 40' slip in Lake Mead, NV. Approximately once a week during the boating season, quagga mussels were manually scraped off from structures submerged in the water in the slip including buoys, ropes, Hydro-lift for the boat, and hoses to remove quagga mussels before using the equipment.

In an attempt to reduce the above-described maintenance and avoid the threat of quagga mussels invading a boat's engine via the intake manifold that cools the engine, thereby fouling the workings therein, two apparatuses made in accordance with Example 1, were hung in the lake at a depth of 3 to 4 feet proximate either side of a ski boat's motor in the 40' slip. The apparatuses were weighed down with rocks to keep them in place. Water temperatures in Lake Mead at that depth range from mid 80's in the summer to near freezing in the winter. The apparatuses and ski boat were left undisturbed for about 6 weeks. After about 6 weeks, no quagga mussels were observed on or near the boat, equipment, or anywhere in the area surrounding the motor. The apparatuses were left in the same position for another 2 months. After another 2 months, no quagga mussels were observed on or near the boat, equipment, or anywhere in the area surrounding the motor. After approximately 14 weeks in the water, a large area having approximately a 10'-12' radius around the apparatus and around the motor was devoid of mussels. Scraping equipment to remove quagga mussels was therefore avoided, along with the threat of infestation of the engine.

Example 5

Comparative Example with Zero Valent Iron

A disk is made with zero valent iron particles from KDF in a process similar to Example 1. The disk is suspended in water having zebra mussels in a process similar to Example 4. The zero valent iron treated disks is used to treat water and is found not to be effective in repelling mussels.

Example 6

Copper Leaching Test

A pouch made in Examples 1 and 2 above was tested to determine the amount of copper leaching in a sample of water drawn from Idaho's Snake River near Idaho Falls.

A 15 gallon test tank was filled with 15 gallons of the sample water. A common single speed fish tank pump was introduced for circulating water in the tank to simulate a current that might be found in a lake or river. The pouch was suspended using a parachute cord in the middle of the sample water-filled tank. A 1 liter sample of water was taken from the tank before the trial to measure the base copper level in the water. The pump was turned on. After 45 days, another sample was taken from the tank. The samples were tested by IAS Envirochem in Pocatello, Id., using standard sampling methods. The samples were refrigerated at 4° C. before introducing the samples to an inductively coupled plasma mass spectrometer where the copper level in each sample was measured. The sample taken from the tank before the trial contained 0.001 mg/L (ppm) of copper. The sample taken from the tank after 45 days contained 0.194 mg/L of copper.

The EPA has indicated that the copper level based on maximum contaminant level goals (MCLG) should not exceed 1.3 mg/L or 1.3 ppm. Example 6 shows that the amount of copper that leached from the apparatus was significantly lower than EPA limits in a very small sample of water. Samples taken from large bodies of water where the apparatus is in use is expected to have a far lower concentration of copper.

What is claimed is:

1. A method comprising
repelling or preventing infestation of mollusks in a body of water infested with mollusks or at risk of infestation by mollusks with a repellant comprising copper and zinc fines adhered to a reticulated foam substrate;
wherein the repelling or preventing step further comprises:
contacting the repellant with the body of water for a time sufficient to repel or prevent infestation by the mollusks; and
wherein the zinc solubilizes during the contacting step in an amount sufficient to repel or prevent infestation by said mollusks; and
wherein the copper remains substantially adhered to the reticulated foam substrate during the contacting step.

2. The method of claim 1,
wherein the zinc is present in the copper and zinc fines in an amount greater than the maximum saturation concentration of zinc in a copper and zinc solid solution.

3. The method of claim 2,
wherein the weight ratio of zinc/copper in the copper and zinc fines is greater than about 43/57 weight ratio.

4. The method of claim 1,
wherein the mollusks are zebra mussels or quagga mussels.

5. The method of claim 1,
wherein the body of water is infested with zebra mussels or quagga mussels.

6. The method of claim 1,
wherein the zinc is present in the copper and zinc fines in an amount greater than the maximum saturation concentration of zinc in a solid solution of copper and zinc.

7. The method of claim 1,
wherein the copper and zinc fines are adhered to the reticulated foam substrate with a water resistant adhesive.

8. The method of claim 1,
wherein the body of water is proximate a marina.

9. The method of claim 1,
wherein the body of water is proximate a pylon, channel breakwalls, locks, or docks that are in the water.

10. The method of claim 4,
wherein the body of water contains a bridge therein and the repellant is positioned proximate the bridge.

* * * * *